United States Patent
Togashi et al.

(10) Patent No.: US 8,094,298 B2
(45) Date of Patent: Jan. 10, 2012

(54) METHOD FOR DETECTING PARTICLES AND DEFECTS AND INSPECTION EQUIPMENT THEREOF

(75) Inventors: Takahiro Togashi, Mito (JP); Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/574,185

(22) Filed: Oct. 6, 2009

(65) Prior Publication Data

US 2010/0020315 A1      Jan. 28, 2010

Related U.S. Application Data

(63) Continuation of application No. 12/266,079, filed on Nov. 6, 2008, now Pat. No. 7,619,729, which is a continuation of application No. 11/822,330, filed on Jul. 5, 2007, now Pat. No. 7,456,948.

(30) Foreign Application Priority Data

Jul. 7, 2006   (JP) .................................. 2006-187351

(51) Int. Cl.
*G01N 21/00*   (2006.01)
*G03B 242/02*   (2006.01)
*H01J 37/304*   (2006.01)

(52) U.S. Cl. ............... 356/237.3; 356/237.1; 356/237.2; 356/237.4; 250/492.2; 250/559.01

(58) Field of Classification Search .... 356/237.1–237.5, 356/394, 607, 608; 250/559.42, 559.46, 250/372

See application file for complete search history.

(56) References Cited

U.S. PATENT DOCUMENTS

| | | | |
|---|---|---|---|
| 4,587,617 A * | 5/1986 | Barker et al. | ................. 382/149 |
| 4,681,442 A | 7/1987 | Wagner | |
| 4,902,131 A | 2/1990 | Yamazaki et al. | |
| 4,952,058 A | 8/1990 | Noguchi et al. | |
| 4,966,457 A | 10/1990 | Hayano et al. | |
| 5,144,132 A | 9/1992 | Kitakado | |
| 5,245,403 A | 9/1993 | Kato et al. | |
| 5,249,216 A | 9/1993 | Ohsugi et al. | |

(Continued)

FOREIGN PATENT DOCUMENTS

JP   06-167457   6/1994

(Continued)

OTHER PUBLICATIONS

Japanese Office Action issued in Japanese Patent Application No. JP 2006-187351 dated Feb. 22, 2011.

*Primary Examiner* — Sang Nguyen (74) *Attorney, Agent, or Firm* — McDermott Will & Emery LLP (57) ABSTRACT

A method and equipment which includes an illustrated-spot illumination-distribution data table for storing an illumination distribution within an illustrated spot and which calculates a coordinate position for a particle or a defect and the diameter of the particle on the basis of detection light intensity data about the particle or defect and the illustrated-spot illumination-distribution data table. Thus, even when the illumination distribution within the illustrated spot based on an actual illumination optical system is not a Gaussian distribution, the calculation of the particle diameter of the detected particle or defect and the calculation of a coordinate position on the surface of an object to be inspected can be attained with an increased accuracy.

10 Claims, 5 Drawing Sheets

U.S. PATENT DOCUMENTS

| | | | |
|---|---|---|---|
| 5,270,796 A * | 12/1993 | Tokui et al. | 356/394 |
| 5,327,252 A | 7/1994 | Tsuruoka et al. | |
| 5,377,001 A | 12/1994 | Malin et al. | |
| 5,377,002 A | 12/1994 | Malin et al. | |
| 5,410,400 A | 4/1995 | Shishido et al. | |
| 5,436,464 A | 7/1995 | Hayano et al. | |
| 5,486,919 A | 1/1996 | Tsuji et al. | |
| 5,760,416 A | 6/1998 | Tsuchiya | |
| 5,767,974 A * | 6/1998 | Higashiguchi et al. | 356/394 |
| 5,798,829 A | 8/1998 | Vaez-Iravani | |
| 5,903,342 A * | 5/1999 | Yatsugake et al. | 356/237.4 |
| 5,963,726 A | 10/1999 | Rust et al. | |
| 6,122,047 A | 9/2000 | Stover et al. | |
| 6,204,918 B1 | 3/2001 | Isozaki et al. | |
| 6,437,862 B1 * | 8/2002 | Miyazaki et al. | 356/237.2 |
| 6,529,270 B1 | 3/2003 | Bills | |
| 6,618,136 B1 * | 9/2003 | Ishida | 356/239.1 |
| 6,792,359 B2 | 9/2004 | Ninomiya et al. | |
| 6,798,504 B2 | 9/2004 | Sato et al. | |

FOREIGN PATENT DOCUMENTS

| | | |
|---|---|---|
| JP | 11-295229 | 10/1999 |
| JP | 2002-228428 | 8/2002 |

* cited by examiner

SIDE VIEW

FIG.2B

PLAN VIEW

METHOD FOR DETECTING PARTICLES AND DEFECTS AND INSPECTION EQUIPMENT THEREOF

RELATED APPLICATIONS

This application is a Continuation of U.S. patent application Ser. No. 12/266,079, filed on Nov. 6, 2008 now U.S. Pat. No. 7,619,729, which is a Continuation of U.S. patent application Ser. No. 11/822,330, filed on Jul. 5, 2007, now U.S. Pat. No. 7,456,948, claiming priority of Japanese Patent Application No. 2006-187351, filed on Jul. 7, 2006, the entire contents of each of which are hereby incorporated by reference.

BACKGROUND OF THE INVENTION

The present invention relates to a detecting method and inspection equipment. The present invention, in particular, relates a technique for detecting fine particles and defects present on a thin film substrate, a semiconductor substrate, a photomask and so on. The present invention also concerns a technique suitable for calculating the diameter of a fine particle or defect on a semiconductor wafer substrate or increasing the detection accuracy of a coordinate position of the particle or defect on the surface of an object to be inspected.

In a production line for a semiconductor substrate, a thin film substrate or the like; for the purpose of monitoring the generated dust condition of a manufacturing apparatus, foreign matter or particles deposited on the surface of the semiconductor substrate, the thin film substrate or the like are inspected. For example, with regard to the semiconductor substrate prior to a circuit pattern formation step, it is required to detect fine particles having such fine diameters of several tens of nm or smaller on the substrate. One of prior art techniques for detecting fine defects on the surface of such an inspecting object as a semiconductor substrate is disclosed, for example, in U.S. Pat. No. 5,798,829 (Patent Document 1). In the patent, the surface of a semiconductor substrate is fixedly illuminated with a condensed laser beam (, at which time the illustrated region formed on the surface of the semiconductor substrate by the laser beam will be referred to as the illustrated spot.), scattered light from particles or defects deposited on the semiconductor substrate is detected, and such particles or defects on the entire surface of the semiconductor substrate are inspected through rotation and translational motion of the semiconductor substrate. An ellipsoidal mirror is used for detecting the scattered light, a detection position on the semiconductor substrate is set at a position corresponding to a first focus of the ellipsoid of the mirror, and the light receiving surface of a light receiving element is located at a position corresponding to a second focus of the ellipsoid, so that the scattered light from a particle can be condensed with a wide solid angle and therefore even a fine particle can be detected.

In such a prior art particle/defect inspecting apparatus, in general, the detection resolution of a coordinate at a particle/defect detection position has been restricted by the dimension of the illustrated spot in a sub-scan direction of the illustrated spot. As one of recent prior arts for enabling lightening of such restriction and detection of the position coordinate of the detected particle/defect with a resolution or accuracy better than a distance between adjacent main scan locuses in the sub-scan direction, such a technique is known as disclosed in JP-A-11-295229 (Patent Document 2).

In the aforementioned prior art, from the theoretical ground that an illumination distribution at the focused point of the condensed laser beam follows a Gaussian function, the illumination distribution of illumination light within the illustrated spot on the inspection object is assumed to follow the Gaussian function (or another function similar to the Gaussian function). Thus, results of actual measured values of scattered light at a plurality of points are made to fit with the aforementioned known function, and a peak position and peak intensity of the scattered light are calculated as values seemingly closer to true values with a resolution higher than the resolution of the discrete feed of the main scan and sub-scan. However, the illumination distribution within the illustrated spot in an actual illumination optical system does not always follows the Gaussian function, due to the aberration of the illumination optical system or to the quality of a beam issued from a laser light source. When a difference between the actual illumination distribution of the illustrated spot and the Gaussian function is great, the peak position and peak intensity of the scattered light calculated by the aforementioned method contain a large error, as an obvious matter. Further, when a stage for moving the inspection object in such a manner as to provide rotational motion for the main scan and translational motion for the sub-scan, is used; the locus of the main scan forms not a straight line but part of a circle arc, and the curvature of the arc is smaller than the inner periphery on the inspection object, that is, sharp. As described in the prior art, when data about the scattered light and the illumination distribution of the illustrated spot are compared in a (main scan/sub-scan) coordinate system, the comparison may adversely affect the coordinate detection accuracy when no consideration is paid to the influence of the curvature. In this connection, since the particle/defect inspecting apparatus usually outputs a coordinate value for the detected particle/defect in a form expressed in a Cartesian coordinate system on the inspection object, it is desirable from the viewpoint of its principle to handle it in the Cartesian coordinate system.

SUMMARY OF THE INVENTION

In view of such circumstances, it is therefore an object of the present invention to calculate a peak position and peak intensity of scattered light closer to their true values even when an illumination distribution within an illustrated spot in an actual illumination optical system does not always follow the Gaussian function. Another object of the present invention is to provide a technique for increasing accuracies in the detection of the size of an inspection target such as a particle or a defect and in the detection of a coordinate position on the inspection object.

In accordance with an aspect of the present invention, there is provided a detection method which includes the steps of illuminating the surface of an object to be inspected with light from a light source as an illustrated spot; detecting at least one of beams of the illuminated light scattered, diffracted, and reflected at the illustrated spot, and then converting the detected light to an electric signal; converting the electric signal to digital data; detecting a position on the inspection object corresponding to the converted digital data as inspection coordinate data; determining the presence of a detection target on the surface of the inspection object or in the interior of the inspection object close to its surface on the basis of the electric signal or the digital data; calculating a size of the determined detection target on the basis of the digital data; and calculating a coordinate value for the position on the inspection object on the basis of the inspection coordinate data, wherein the position coordinate value is calculated on the basis of the digital data and illumination distribution data within the illustrated spot.

In accordance with another aspect of the present invention, there is provided inspection equipment which includes an inspection object moving stage for moving an object to be inspected; a light source; an illumination optical system for illuminating the surface of the inspection object with light from a light source in the form of an illustrated spot; a light detection system for detecting at least one of the illuminated light scattered, diffracted, and reflected at the illustrated spot, and converting the detected light to an electric signal; a converter for converting the electric signal to digital data; an inspection coordinate detecting mechanism for detecting a position on the surface of the inspection object corresponding to the converted digital data as inspection coordinate data; an inspection object determination mechanism for determining the presence of an detection target on the basis of the electric signal and the digital data; a particle diameter calculation mechanism for calculating a size of the detection target determined from the digital data; and a detection target coordinate calculation mechanism for calculating a coordinate value for the position on the inspection object on the basis of information from the inspection coordinate detecting mechanism, and wherein the converter has a memory for storing the digital data obtained by sampling the electric signal and illumination distribution data about the illuminated light within the illustrated spot on the inspection object, and the detection target coordinate calculation mechanism calculates the position coordinate of the detection target on the basis of the digital data and the illumination distribution data.

In accordance with a further aspect of the present invention, there is provided inspection equipment which includes an inspection object moving stage for providing a translational motion as its main scan and a translational motion nearly perpendicular to the translational motion of the main scan as its sub-scan, or for providing a rotational motion as its main scan and a translational motion as its sub-scan; a light source; an illumination unit for illuminating the surface of the inspection object with light from the light source as an illustrated spot having a predetermined size on the inspection object; a scattered/diffracted/reflected light detector for detecting part of the illuminated light scattered, diffracted, and reflected on the illustrated spot and converting the detected light to an electric signal; an A/D converter for converting the electric signal to digital data; an inspection coordinate detector for detecting a position on the inspection object at a time corresponding to the converted digital data as inspection coordinate data; a particle/defect determiner for determining the presence of a particle or a defect on the inspection object or in the interior of the inspection object in the vicinity of its surface on the basis of the electric signal or the digital data; a particle diameter calculator for calculating a size of the determined particle or defect on the basis of the digital data; and a particle/defect coordinate calculator for calculating a coordinate value of the position of the particle or defect on or in the inspection object on the basis of information from the inspection coordinate detector. In the inspection equipment, the A/D converter includes a digital data table for storing or saving a plurality of digital data obtained by (1) continuously sampling the electric signal at intervals of a predetermined time and (2) continuously obtained on a main scan focus over a time corresponding at least 2 turns of the inspection object moving stage, and also includes an illustrated-spot illumination-distribution data table for (3) storing or saving a relative illumination distribution of illuminated light within the illustrated spot on the surface of the inspection object in a two-dimensional Cartesian coordinate system having a y axis in a direction of a straight line connected from the rotational center of the inspection object moving stage to the center of the illustrated spot and having an x direction perpendicular to the y axis as two-dimensional matrix data having data divisions divided at intervals of a first spacing in the x axis direction and at intervals of a second spacing in the y axis direction. And (4) the particle/defect coordinate calculator calculates position coordinate value X, Y in a two-dimensional Cartesian coordinate system (X, Y) having the linear symmetrical axis of the determined particle or defect on the inspection object as a Y axis and having a direction perpendicular to the Y axis as an X axis with use of a result from comparison between the digital data table and the illustrated spot illumination distribution data table.

In accordance with yet another aspect of the present invention, (5) the particle diameter calculator calculates a size of the particle or defect with use of a result from comparison between the digital data table and the illustrated spot illumination distribution data table.

In accordance with yet another aspect of the present invention, the digital data table of the above (2) is replaced with (6) a digital data table for storing or saving some of a plurality of the digital data pieces continuously obtained on a main scan locus over a period of time corresponding at least 2 turns of the inspection object moving stage, which are extracted on the basis of information from the particle/defect determiner.

In accordance with a still further aspect of the present invention, a means for obtaining the illustrated spot illumination distribution in the above paragraph (3) includes (7) a technique having an illustrated spot observation camera for measuring a relative illumination distribution in the illustrated spot or (8) a technique having a within-illustrated-spot illumination distribution measuring function of measuring the relative illumination distribution within the illustrated spot with use of the inspection object having a standard particle deposited thereon.

In accordance with an additional aspect of the present invention, (9) the illumination unit is arranged so that at least one of optical conditions, that is, an illustrated spot diameter, an incident angle to the surface of the inspection object, the polarization state of the illuminated light, the wavelength of the light source, and the luminous intensity of the light source, is changed to a plurality of states, and (10) a technique having a plurality of such illustrated spot illumination distribution data tables for storing or saving a plurality of illustrated spot illumination distributions corresponding to the plurality of optical conditions is also included.

In accordance with another aspect of the present invention, (11) a technique for automatically selecting one of the plurality of illustrated spot illumination distribution data tables stored or saved, corresponding to the selected optical condition and for using the selected table upon the inspection is also included with use of the above techniques of (9) and (10).

According to the present invention, the calculation of the size of the detection target and the detection of an coordinate position on the inspection object can be increased in accuracy. The present invention will be detailed below in connection with embodiments of the invention.

Other objects, features and advantages of the invention will become apparent from the following description of the embodiments of the invention taken in conjunction with the accompanying drawings.

DESCRIPTION OF THE INVENTION

The present invention can be embodied as a technique for detecting the presence of a fine particle or defect on or in a thin film substrate such as a thin film transistor substrate or in a semiconductor substrate, a photomask, or the like. The present invention will be explained as a technique for suitably increasing the accuracy of calculating the diameter of a fine particle or defect on a semiconductor wafer substrate or the accuracy of detecting a coordinate position thereof on the surface of an object to be inspected, in connection with a first embodiment of the present invention by referring to the accompanying drawings.

Figure 1:
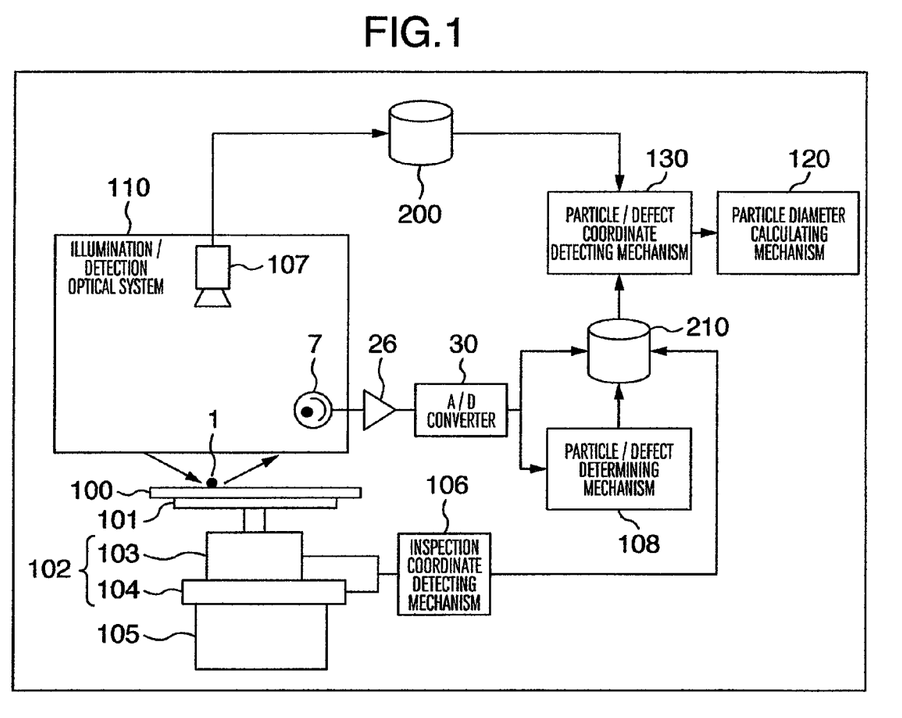
FIG. 1 shows an arrangement of particle/defect inspection equipment in accordance with a first embodiment of the present invention.
Figure 2A:
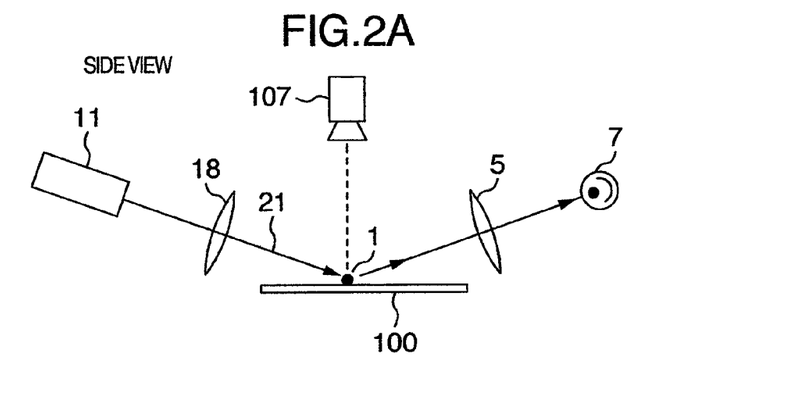
FIG. 2A is a side view of a structure of an optical system in the first embodiment.
Figure 2B:
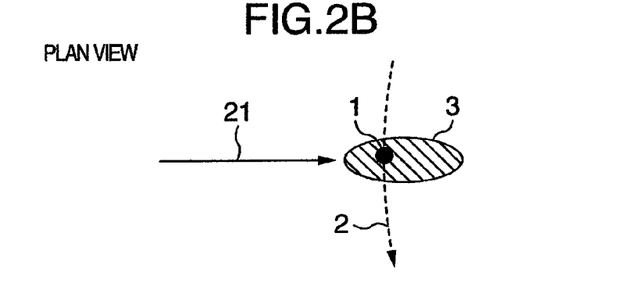
FIG. 2B is a plan view of the structure of the optical system in the first embodiment.

As shown in FIG. 1, a semiconductor wafer 100 as an object to be inspected is vacuum sucked on a chuck 101, and the chuck 101 is mounted on an inspection object moving stage 102 including a rotary stage 103 and a translational motion stage 104, which in turn is mounted on a Z stage 105. An illumination/detection optical system 110 disposed above the semiconductor wafer 100 is shown in FIG. 2. More specifically, as a light source 11 for illuminated light, a laser light source is used. Light emitted from the light source 11 enters an illumination lens 18, exits the lens as an illustration beam 21, and forms an illustrated spot 3 of a predetermined size on the inspection object. The illuminated light is, for example, of a P polarization light, and is arranged so as to be obliquely incident to a crystal Si nearly with a Brewster angle on the surface of the semiconductor wafer 100 as the inspection object. For this reason, the illustrated spot 3 has a nearly elliptical shape, and the illustrated spot is defined herein to have an illuminance at a given position inside of the contour line of the illustrated spot, and the illuminance is expressed by $1/e^2 \times$(an illuminance at the center of the illustrated spot) (e: the base of natural logarithm). The widths of the illustrated spot in its long and short axis directions are denoted by reference symbols d1 and d2 respectively.

Figure 3:
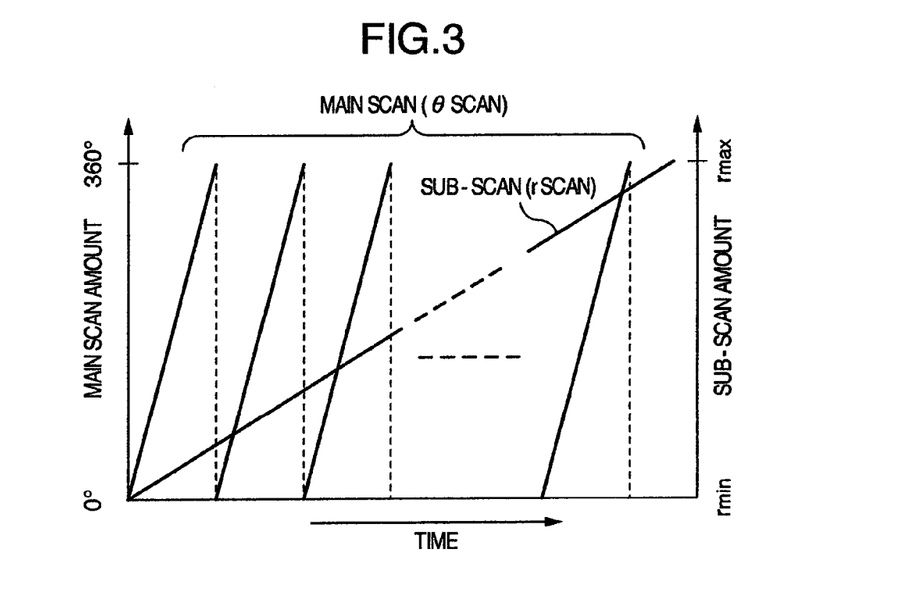
FIG. 3 is a diagram for explaining a method for driving an inspection object moving stage for spiral scanning in the embodiment of the invention.

As shown in FIG. 3, the inspection object moving stage 102 is moved by changing a rotational motion θ as its main scan and a translational motion r as its sub-scan with time, so that the illustrated spot 3 is spirally scanned on the nearly entire surface of the semiconductor wafer 100. While the rotary stage rotates by one turn, the sub-scan is shifted by Δr. When Δr>d1, no illuminating light is applied onto the semiconductor wafer 100 in the spiral scanning and a gap region not to be inspected takes place. To avoid this, the system is set so as to meet a relation Δr<d1. In the present embodiment, the scanning of the illustrated spot 3 is carried out from the inner periphery of the semiconductor wafer 100 toward the outer periphery thereof. However, the scanning direction may be reversed as necessary. In the present embodiment, the rotary stage 103 is driven nearly at a constant angular velocity and the translational motion stage 104 is driven nearly at a constant linear speed, throughout the nearly full region from the inner periphery of the semiconductor wafer 100 to the outer periphery thereof. As a result, the relative movement linear speed of the illustrated spot 3 to the surface of the semiconductor wafer 100 at the outer periphery becomes larger than that at the inner periphery. For the purpose of detecting a main scan coordinate position θ and a sub-scan coordinate position r during inspection, the inspection object moving stage 102 is provided with an inspection coordinate detecting mechanism 106. In the present embodiment, an optical reading rotary encoder is used to detect the main scan coordinate position θ and an optical reading linear encoder is used to detect the sub-scan coordinate position r. However, another detection principle may be employed, so long as an angle or a position on a line can be accurately detected. A condensing lens 5 is arranged so as to condense the scattered light with a low elevation angle, that is, so as to be capable of efficiently trapping light scattered by a fine particle, for example, by Rayleigh scattering.

As shown by a particle movement locus 2 in the plan view of FIG. 2B, in this arrangement, a particle 1 passes through the illustrated spot 3 and thus a scattered light signal is obtained from an optical detector 7. Although a photomultiplier tube is employed as the optical detector 7 in the present embodiment, an another optical detector based on another detection principle may be used so long as the detector can detect light scattered by a particle with a high sensitivity.

Further, in order to obtain an illumination distribution within the illustrated spot 3, the present embodiment includes an illustrated spot observation camera 107 for observing the illustrated spot 3 nearly from the above side in a vertical direction; and also includes an illustrated-spot illumination-distribution data table 200 for acquiring a relative illumination distribution from the illustrated spot observation camera 107 in a two-dimensional Cartesian coordinate system having a y axis in a direction of a straight line connected from the rotational center of the rotary stage 103 to the center of the illustrated spot 3 on the surface of the inspection object and having an x axis perpendicular to the y axis and for storing or saving the acquired relative illumination distribution as two-dimensional matrix data having data divisions divided at intervals of a first spacing in the x direction and at intervals of a second spacing in the y direction. In the present embodiment, the illustrated spot observation camera 107 has 640 pixels in the y direction and 480 pixels in the x direction, and the size of one pixel is set at nearly one micrometer when converted on the surface of the semiconductor wafer 100. However, the pixel numbers and the resolution may be changed so long as the changed pixel numbers and resolution can allow the entire illustrated spot 3 to be imaged with a sufficient resolution. Desirably, the resolution is set to be within 5 micrometers. With respect to the semiconductor wafer 100 to be actually inspected, even when a laser beam is applied to such a region of the wafer that has a small surface roughness and has no particle/defect deposited thereon, only a very weak scattered light is obtained and an image for the illustrated spot 3 cannot be, in many cases, confirmed with use of the illustrated spot observation camera 107. In the present embodiment, such an illustrated spot observing wafer or a standard specimen for illustrated spot observation having a material and/or outer shape different from the wafer but capable of being treated equivalently is previously prepared that has a sufficiently flat surface and a uniform surface roughness, the surface roughness enables the relative illumination distribution within the illustrated spot 3 to be sufficiently imaged with use of the illustrated spot observation camera 107 when the specimen surface is subjected to the laser beam. Before starting inspecting the semiconductor wafer 100, the illustrated spot observing wafer or the illustrated spot observing standard specimen is imaged at the position of the semiconductor wafer 100 so that a relative illumination distribution within the illustrated spot 3 is previously imaged with use of the illustrated spot observation camera 107 and previously stored or saved in the illustrated-spot illumination-distribution data table 200 as two-dimensional matrix data.

Explanation will next be made as to signal processing in the present embodiment. Scattered light from the optical detector 7 is amplified by an amplifier 26, and then sampled by an A/D converter 30 at intervals of a predetermined time ΔT to be converted to digital data. The digital data is compared with a predetermined detection threshold by a particle/defect determining mechanism 108. When the digital data is not smaller than the threshold, the particle/defect determining mechanism 108 determines that the digital data comes from a particle/defect and generates particle/defect determination information. The digital data is passed to the particle/defect determining mechanism 108, and at the same time, also sequentially stored or saved in a digital data table 210. For associating the stored digital data pieces with inspection coordinate positions, the digital data table 210 stores each digital data piece together with the inspection coordinate value corresponding to its generated time. With respect to the digital data for which the particle/defect determining mechanism 108 generates the particle/defect determination information, not only the inspection coordinate value but the particle/defect determination information is also stored. The digital data table 210 in the present embodiment has such a large capacity as to be capable of storing all the digital data acquired for 3 turns of the inspection object moving stage 102. When the amount of saved digital data exceeds the 3-turn data, the saved data is sequentially deleted in the older (earlier) order of stored time and instead, the latest digital data is stored or saved.

Figure 4:
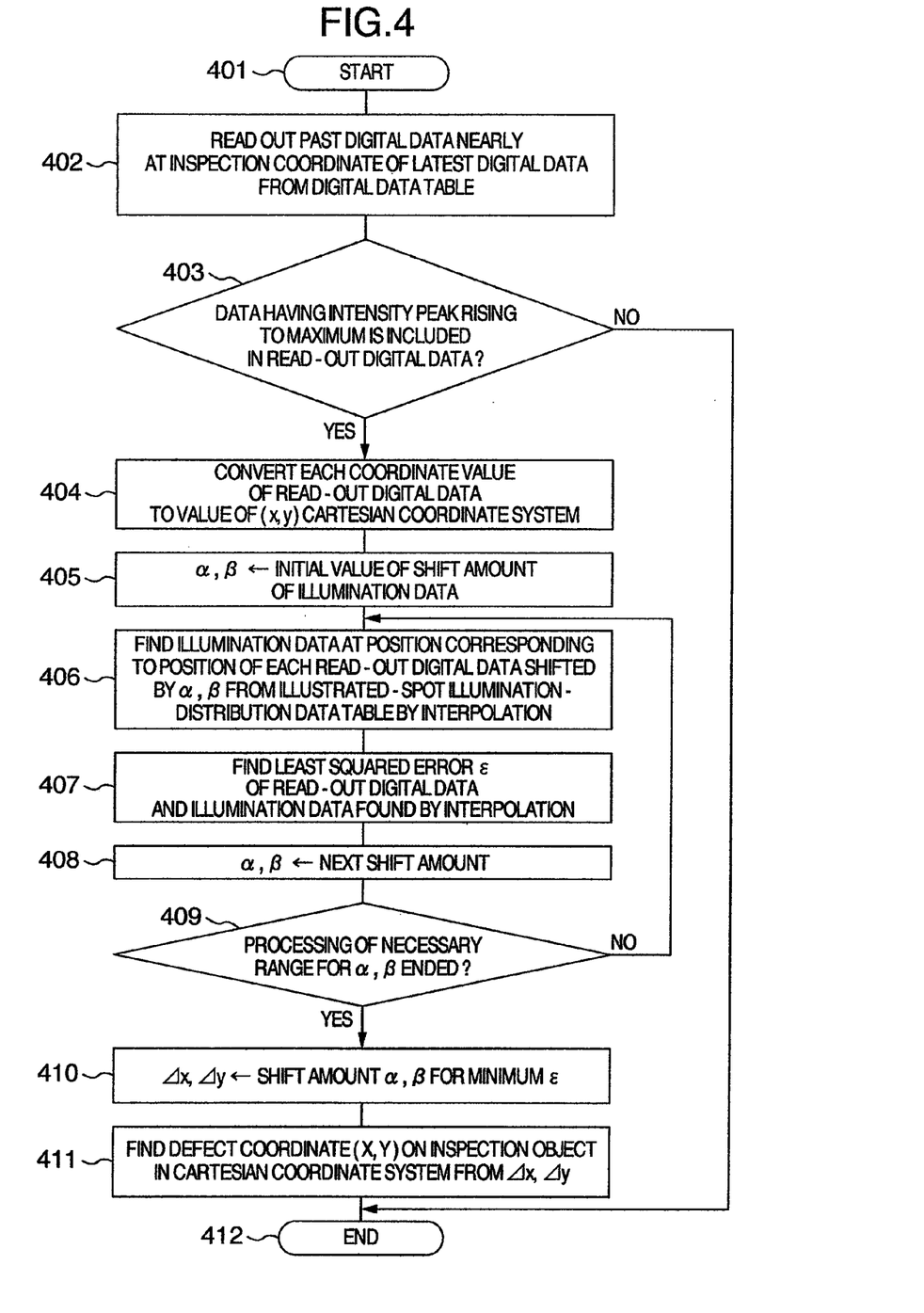
FIG. 4 is a flow chart for explaining the operation of the embodiment of the present invention.

In the present embodiment, a particle/defect coordinate detecting mechanism 130 performs its operation according to a flow chart of FIG. 4 each time the latest digital data is written in the digital data table 210, and calculates position coordinate values X, Y in a two-dimensional Cartesian coordinate system (X, Y) having a Y axis corresponding to a direction of a linear symmetric axis of the detected particle or defect on the surface of the inspection object and having an X axis perpendicular to the Y axis.

The above processing operation will be explained. It is assumed that the rotary stage 103 rotated by an angle of Δθ during one sampling interval, a combination of a main scan coordinate value and a sub-scan coordinate value in the latest digital data is expressed by inspection coordinate value $(r_{0,0}, \theta_{0,0})$, and the value of the latest digital data is expressed by $D_{0,0}$. It is also assumed that digital data at a position spaced by m×Δθ (m being integer and the past being toward the negative going direction) in the main scan direction from the inspection coordinate value of the latest digital data and spaced by n×Δr (n being an integer and the past being toward the negative going direction) in the sub-scan direction has inspection coordinate value $(r_{m,n}, \theta_{m,n})$, and the value of the digital data is expressed by $D_{m,n}$. It is further assumed in the inspection coordinate value that at most (2k+1) (k: natural number) digital data pieces are generated during a time of passage of a particle or defect through the width d2 of the illustrated spot 3 in its short axis direction. First, the processing starts from a step 401 in FIG. 4.

(Processing 1): Digital data $D_{i,j}$ satisfying a relation of $-2k \leq i \leq 0$ (i, j: each integer) for each j in a relation of $-2 \leq j \leq 0$ is read out from a past digital data stored in the digital data table 210 (a step 402 in FIG. 4).

(Processing 2): Of the $D_{i,j}$ read out in the (Processing 1), when $D_{-k,-1}$ has no defect determination information attached thereto, the system performs no operation and terminates its operation (, which corresponds to a case when the system determines 'No' in a step 403 in FIG. 4 and goes to a step 412 of 'End').

(Processing 3): Of the $D_{i,j}$ read out in the (Processing 1), the system searches for maximum digital data $D_{i0,j0}$. When a relation of $D_{i0,j0}=D_{-k,-1}$ is not satisfied, the system performs no operation and terminates its operation (, which corresponds to a case when the system determines 'No' in the step 403 in FIG. 4 and goes to the 'End' step 412 in FIG. 4).

(Processing 4): The system converts the inspection coordinate value $(r_{i,j}, \theta_{i,j})$ of each digital data $D_{i,j}$ read out in the (Processing 1) into coordinate value $(x_{i,j}, y_{i,j})$ in the two-dimensional Cartesian coordinate system (x,y) having a y axis corresponding to a direction of a straight line connected from the inspection coordinate value $(r_{-k,-1}, \theta_{-k,-1})$ of $D_{-k,-1}$ to the rotational center of the rotary stage, having an x axis perpendicular to the y axis, and having an origin (0,0) corresponding to a position $(r_{-k,-1}, \theta_{-k,-1})$. The conversion is carried out according to equations which follow.

$$x_{i,j}=r_{i,j}\times\cos\theta_{i,j}-r_{-k,-1}\times\cos\theta_{-k,-1}$$

$$y_{i,j}=r_{i,j}\times\sin\theta_{i,j}-r_{-k,-1}\times\sin\theta_{-k,-1}$$

In the inspection object moving stage for providing rotational motion as its main scan and translational motion as its sub-scan, the main scan locus 6 forms part of a circle arc and the curvature of the arc in the inner periphery on the inspection object is smaller than the curvature of the arc in the outer periphery, that is, the arc in the inner periphery is sharp. Thus, when comparison between scattered light data and the illumination distribution of an illustrated spot is made in a coordinate system (main scan, sub-scan) as in the prior art, no consideration of the influences of the aforementioned curvature causes a coordinate detection accuracy to be adversely affected. However, when data on the scattered light is converted to data in the Cartesian coordinate system and then treated as in the above case, a constant coordinate detection accuracy can be advantageously obtained through unique calculation even at a given position on the inspection object (, which corresponds to a case when the system determines 'Yes' in the step 403 and goes to a step 404 in FIG. 4).

(Processing 5): When data about a relative illumination distribution in the illustrated spot 3 stored in the illustrated-spot illumination-distribution data table 200 is parallelly moved in the two-dimensional Cartesian coordinate system (x,y), the system calculates and evaluate whether the data optimally matches two-dimensional array data of the digital data $D_{i,j}$ at the coordinate value $(x_{i,j}, y_{i,j})$ in the two-dimensional Cartesian coordinate system (x,y), and finds a parallel movement Δx in the x axis direction and a parallel movement Δy in the y axis direction in the optimum state. The above evaluation and calculation are carried out in the following steps (corresponding to a case when the system goes to steps 405 to 410 in FIG. 4).

(Step 1): The system finds relative illumination distribution data $I_{i,j}$ in the illustrated spot 3 corresponding to a position obtained by shifting a position of the data $D_{i,j}$ by α in the x axis direction and by β in the y axis direction by interpolation from the illustrated-spot illumination-distribution data table 200. At this time, it is preferable from the viewpoint of securing an accuracy upon the interpolation that a data spacing Δη (1 micrometer in the present embodiment) in the y axis direction of the illustrated-spot illumination-distribution data table 200 is a data spacing in a j direction of $D_{i,j}$, that is, Δr be divisible by Δη. It is desirable that the resolution of the illustrated spot observation camera 107 be nearly 5 micrometers or smaller when converted on the surface of the semiconductor wafer 100. However, when the resolution is lower than nearly 5 micrometers, it is preferable to previously interpolate an image obtained from the illustrated spot observation camera 107 to increase the pixel resolution and then to store it in the illustrated-spot illumination-distribution data table 200.

(Step 2): From an equation of $D_{i,j}=p \times I_{i,j}+q$, the system finds p, q which are best suitable for $D_{i,j}$ and $I_{i,j}$ by the least squares method.

(Step 3): The system finds an error sum of squares in the state of a result of the (Step 2), that is, a sum ε of all combinations of i and j of squares of $(D_{i,j}-I_{i,j})$.

(Step 4): The system calculates (Step 1) to (Step 3) for changed values of α and β, and sets Δx and Δy for smallest ones of error sums ε of squares of the values of α and β.

(Processing 6): The inspection coordinate value $(r_{-k,-1}, \theta_{-k,-1})$ for $D_{-k,-1}$ can be converted to a position coordinate value $X_{-k,-1}, Y_{-k,-1}$ in the two-dimensional Cartesian coordinate system (X,Y) having a Y axis corresponding to a direction of a linear symmetric axis on the surface of the inspection object, having an X axis perpendicular to the Y axis, and having an origin (0,0) corresponding to the rotational center of the rotary stage 103, by converting it according to equations which follow.

$$X_{-k,-1}=r_{-k,-1} \times \cos \theta_{-k,-1}$$

$$Y_{-k,-1}=r_{-k,-1} \times \sin \theta_{-k,-1}$$

The system calculates a particle/defect coordinate calculation result 9 at accurate coordinate positions X, Y of the detected particle or defect, by adding Δx, Δy obtained in the (Processing 5) to the converted result of the (Processing 6), that is, by finding $X=X_{-k,-1}+\Delta x$ and $Y=Y_{-k,-1}+\Delta y$ (, which corresponds to a step 411 in FIG. 4).

Figure 5:
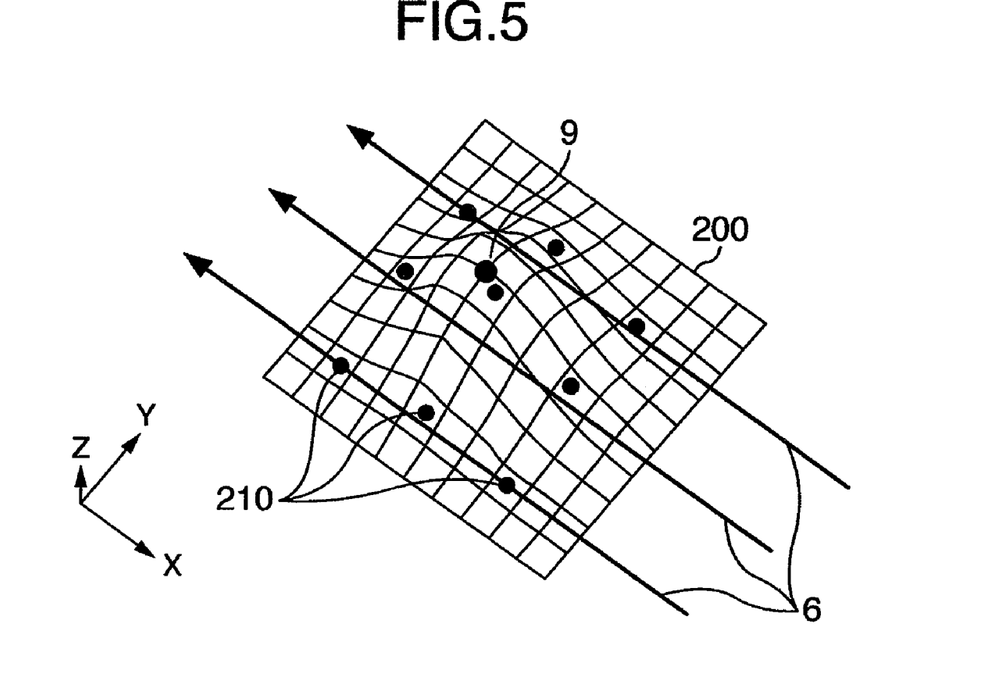
FIG. 5 is a diagram for explaining a method of comparing a digital data table and an illustrated spot illumination distribution data table in the embodiment of the present invention.

FIG. 5 shows a relation between the digital data table 210 and the illustrated-spot illumination-distribution data table 200 in comparison. Arrows in FIG. 5 show 3 main scan locuses 6.

In the present embodiment, the origin of an eventually found defect coordinate (X,Y) is set at the rotational center of the rotary stage 103, that is, at the center of the semiconductor wafer 100. However, when the origin is set at another position, it is only required to shift the calculation by the corresponding amount parallelly. When there is a shift between the rotational center of the rotary stage 103 and the center of the semiconductor wafer 100 and it is desired to correct the shift, it is similarly only required to shift the calculation by the corresponding amounts corresponding to components of the center shift in the x and y axis direction parallelly. When it is desired to correct an error when the semiconductor wafer 100 is mounted on the rotary stage 103 with a tilt Δξ to the origin of a rotational angle of the rotary stage 103, it is only required to correct $\theta_{-k,-1}$ in the equations in the above (Processing 6) by the corresponding amount.

When the accurate coordinate position (X,Y) of the detected particle or defect in the (Processing 6) is found, a particle diameter calculating mechanism 120 next corrects maximum digital data $D_{-k,-1}$ in actual measured values for the particle or defect according to an equation which follows, with use of a value $I_{-k,-1}|_{0,0}$ of $I_{-k,-1}$ when α and β are set at zero in the above (Processing 5) and a value of $I_{-k,-1}|_{\alpha,\beta}$ of $I_{-k,-1}$ for α and β when the error sum of squares become minimum, and calculates the size of the detected particle or defect.

$$D_{-k,-1}'=(I_{-k,-1}|_{\alpha,\beta}/I_{-k,-1}|_{0,0}) \times D_{-k,-1}$$

Unlike the size of the particle/defect directly found using maximum digital data $D_{-k,-1}$ in actually measured values thereof, since the calculated result is calculated using the value of an illuminance seemingly closest to the illuminance of the particle/defect passage position on the basis of the relative position of the particle/defect passed through the illustrated spot 3, the result can be obtained with a higher accuracy.

In the present embodiment, the particle/defect determining mechanism 108 determines the presence of a particle or defect by comparing digital data obtained from the A/D converter 30 with a predetermined threshold. However, in place of directly obtaining digital data from the A/D converter 30, digital data stored in the digital data table 210 may be read out and used for the above determination. Or in place of it, the particle/defect determining mechanism may determine the presence of the particle or defect by comparing an output electric signal from the amplifier 26 with a predetermined threshold voltage.

In the present embodiment, all the digital data acquired for 3 turns of the inspection object moving stage 102 are arranged to be stored in the digital data table 210. However, as will be easily understood from the (Processing 1) to the (Processing 6), any digital data table is employed so long as the table can store all the digital data acquired for at least 2 turns of the inspection object moving stage 102 and can store data about (2k+1) or more points.

The values of digital data for use of the particle/defect determining mechanism 108 not larger than a predetermined detection threshold are meaningless when compared with relative illumination distribution data within the illustrated spot 3. Thus in place of such an arrangement as to hold all the digital data as in the above embodiment, only ones of digital data pieces determined by the particle/defect determining mechanism 108 not to be smaller than a predetermined detection threshold may be stored or saved in the digital data table 210. In this case, in the (Processing 1) to (Processing 6), $D_{i,j}$ not present in the digital data table 210 are not used for the comparative calculation and therefore removed therefrom. In addition to digital data determined by the particle/defect determining mechanism 108 not to be smaller than the predetermined detection threshold, when digital data before and after the determined digital data, that is, digital data earlier by at least one sampling interval or more and later at least by one sampling interval or more at times of the digital data determined by the particle/defect determining mechanism 108 to have exceeded the above threshold, and the inspection coordinate data corresponding to the digital data are arranged to be included in the table; even when the threshold is not set to be sufficiently small, such a situation that only excessively large or small digital data are stored in the table can be preferably avoided.

The optical system in the present embodiment incorporates the illustrated spot observation camera 107. However, when relative illumination distribution data within the illustrated spot 3 is acquired with use of a means different from the observation camera or when the relative illumination distribution data within the illustrated spot 3 is once acquired with use of the illustrated spot observation camera 107 and stored in the illustrated-spot illumination-distribution data table 200 and thereafter it is unnecessary to use the illustrated spot observation camera 107, the optical system in the present embodiment may be arranged not to always include the illustrated spot observation camera 107. As a method of acquiring the relative illumination distribution data within the illustrated spot 3 with use of a means other than the illustrated spot observation camera 107, there is a method of measuring the relative illumination distribution within the illustrated spot with use of a semiconductor wafer having a standard particle deposited thereon.

Figure 6:
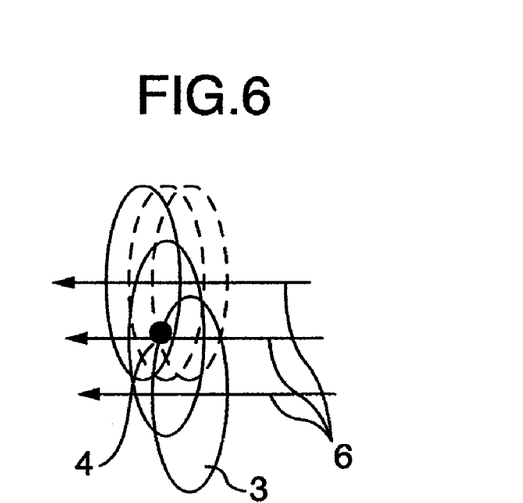
FIG. 6 shows a scanning pattern of a standard particle in the embodiment of the present invention.

FIG. 6 shows a scan pattern of the illustrated spot 3 when the surface of a semiconductor wafer is inspected and attention is paid to a single standard particle 4. In the illustrated example, light passed through the illustrated spot 3 and scattered by the standard particle 4 is sampled in the sub-scan (r) direction at continually 3 or more points on 3 (in this example) main scan (θ) locus and on each of 3 main scan locuses 6 to acquire at least 9 (in total) scattered light intensity data pieces from the single standard particle 4. With respect to each of the scattered light data pieces of the standard particle acquired through the above process, when the coordinate value of the inspection object moving stage at the time point of sampling each data piece is converted to a coordinate value in the two-dimensional Cartesian coordinate system (x,y) having a y axis corresponding to a direction of a straight line connected from the rotational center of the rotary stage 103 to the center of the illustrated spot 3 and having an x axis perpendicular to the y axis, the relative illumination distribution data within the illustrated spot 3 can be obtained. The present invention may be embodied by storing or saving the relative illumination distribution within the illustrated spot measured using an inspection object having such a standard particle deposited thereon in the illustrated-spot illumination-distribution data table 200 as two-dimensional matrix data. In FIG. 6, for easy understanding of the explanation of the present invention, explanation has been made in connection with the case where the above data are acquired through the 3 main scan locuses 6. In an actual application, however, it is desirable that the data interval Δr in the sub-scan direction be divisible by Δη so that the locality of the illumination distribution within the illustrated spot 3 can be sufficiently resolved and that the data interval be set at nearly 5 micrometer or less when converted on the surface of the semiconductor wafer 100. When the resolution is lower than the above value, the data is previously interpolated to increase the pixel resolution, and then stored in the illustrated-spot illumination-distribution data table 200.

Figure 7A:
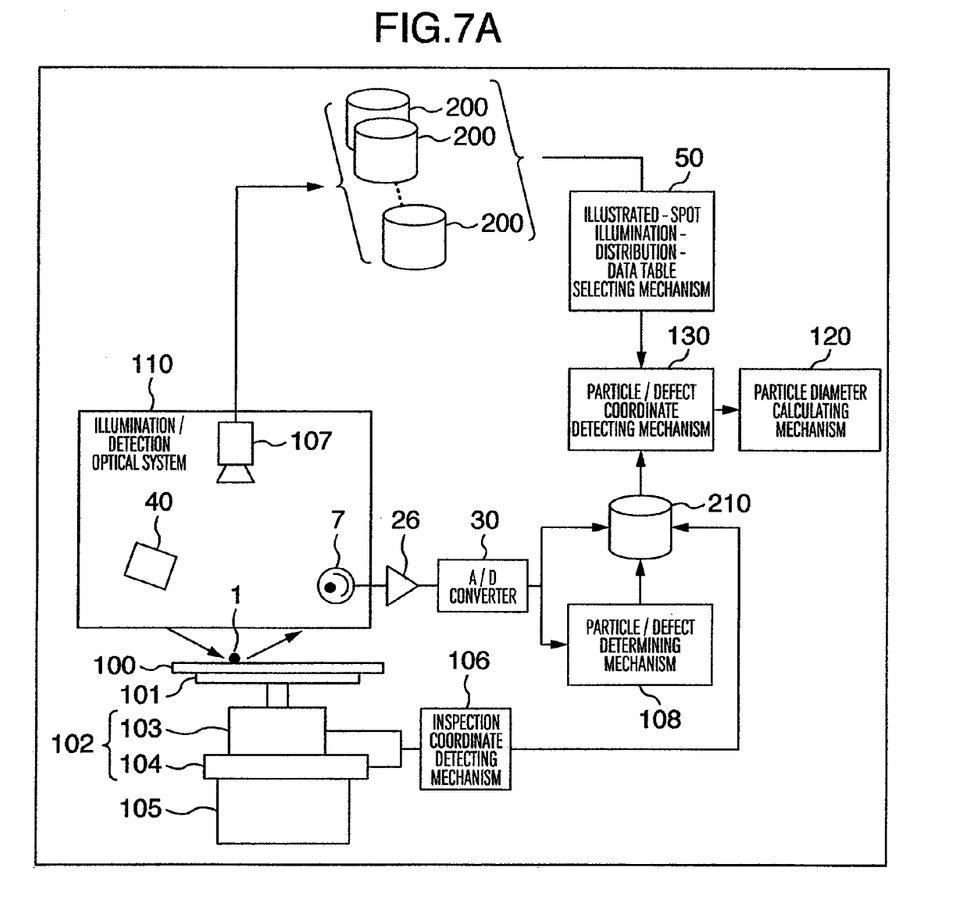
FIG. 7A shows an arrangement of particle/defect inspection equipment in accordance with a second embodiment of the present invention.
Figure 7B:
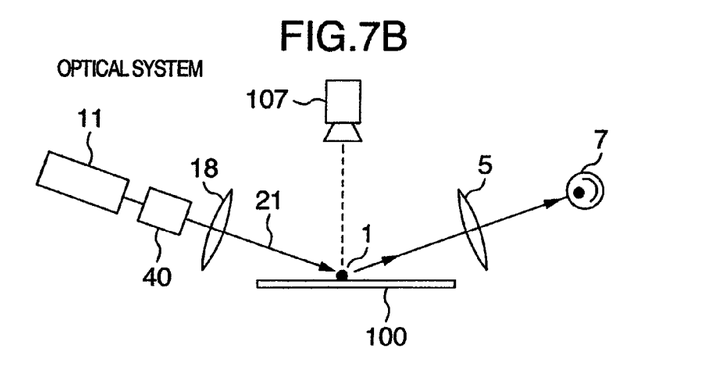
FIG. 7B is a side view of a structure in an optical system in the second embodiment of the present invention.

By referring to FIGS. 7A and 7B, explanation will be made as to a second embodiment of the present invention. The second embodiment is the same as the first embodiment of the present invention; except that an illumination optical condition changeover mechanism 40 for switching between the optical conditions of illuminating light is provided in the illumination/detection optical system 110, a plurality of the illustrated-spot illumination-distribution data tables 200 are provided, and an illustrated-spot illumination-distribution-data table selecting mechanism 50 for automatically selecting one of the plurality of illustrated spot illumination distribution data tables conforming to the set conditions of the illumination optical condition changeover mechanism 40 is provided. Therefore explanation of the same parts is omitted. More specifically, the illumination optical condition changeover mechanism 40 has a mechanism for switching among the P-, S- and circular-polarization directions of the illustration beam 21 and a mechanism for switching among a plurality of sizes of the illustrated spot. In the present embodiment, under conditions that the wafer for illustrated spot observation or a standard specimen for illustrated spot observation is previously put at the position of the semiconductor wafer 100 before the inspection of the semiconductor wafer 100 is started and that the illumination optical condition changeover mechanism 40 is set at one optical condition; the relative illumination distribution within the illustrated spot 3 is imaged with use of the illustrated spot observation camera 107, and stored or saved in one of the plurality of illustrated-spot illumination-distribution data tables 200 as two-dimensional matrix data. The above operation is repeated by changing the optical conditions by a number of times corresponding to combinations of a plurality of optical conditions of the illumination optical condition changeover mechanism 40 or by a number of times corresponding to necessary combinations thereof. When a necessary number of such illustrated-spot illumination-distribution data tables 200 are prepared for all the combinations of the plurality of optical conditions of the illumination optical condition changeover mechanism 40, the semiconductor wafer 100 gets ready for its inspection. In the actual inspection of the semiconductor wafer, an operator selects and sets the illumination optical conditions suitable for the inspection purpose and starts inspecting the wafer. At this time, the illustrated-spot illumination-distribution-data table selecting mechanism 50 automatically sects one of the illustrated-spot illumination-distribution data tables 200 on the basis of the optical conditions switched by the illumination optical condition changeover mechanism 40 according to the illumination optical conditions selected and set by the operator. In the arrangement of the first embodiment, only the single illustrated-spot illumination-distribution data table 200 is provided. Thus, when new illustrated spot illumination distribution data becomes necessary, it is required to discard data already stored in the illustrated-spot illumination-distribution data table 200 at that time point and to externally enter new illustrated spot illumination distribution data each time, or it is required to again measure the illustrated spot illumination distribution data with use of the illustrated spot observation camera 107. However, the present embodiment includes a plurality of illustrated spot illumination distribution data tables capable of storing illustrated spot illumination distribution data about all or some of combinations of the plurality of illumination optical conditions. Accordingly, when the illustrated spot illumination distribution data are previously once stored in the plurality of illustrated spot illumination distribution data tables, it is only required to advantageously select one of the illustrated-spot illumination-distribution data tables 200 corresponding to the selected and set illumination optical conditions while eliminating the need for rewriting it with new illustrated spot illumination distribution data. The illumination optical condition changeover mechanism 40 functions to switch among a plurality of polarization conditions of the illustration beam 21 and among a plurality of sizes of the illustrated spot in the present embodiment. As optical conditions other than the above, however, when the illuminating light can have a plurality of incident angles or when the light source 11 can emits a plurality of wavelengths of light, the mechanism 40, may include a mechanism for switching among a plurality of wavelengths or the like. Even when a plurality of the illustrated-spot illumination-distribution data tables 200 associated with all or some of combinations of the plurality of optical conditions are provided, it will be easily seen that effects similar to the above can be obtained and thus such an arrangement is also possible, as a matter of course.

In this way, in the present embodiment of the present invention, even when the illumination distribution within the illustrated spot in the actual illumination optical system does not always follow the Gaussian function, a scattered light peak position closer to the true value of the detected particle or defect and a peak intensity can be calculated, which can lead to increase in the accuracy of particle diameter calculation of the particle or defect or in the accuracy of coordinate position detection on the surface of the inspection object.

When an illustrated spot illumination distribution actually measured in the inspection is used, accurate inspection can be achieved even when the illustrated spot illumination distribution is varied with a disturbance during the inspection. When an illustrated spot illumination distribution actually measured prior to the inspection is used, further, accurate inspection can be realized even when the illustrated spot illumination distribution is varied with a change with time after the inspection equipment is installed. In addition, after inspection is carried out with use of the illustrated spot illumination distribution in the previous inspection, it is also possible to correct an inspected result using the actually-measured illustrated spot illumination distribution. In this case, the inspection equipment can advantageously cope with the malfunction or failure of the device for measuring the illustrated spot illumination distribution before the inspected result or during the inspection.

Features of the present invention will be exemplified.

Feature 1: A particle/defect detecting method includes an inspection object moving stage nearly continuously moved in both main scan and sub-scan directions for providing a rotational motion in main scan and a translational motion in sub-scan; a light source; an illumination means for illuminating a surface of an object to be inspected with light from the light source as an illustrated spot of a predetermined size; a scattered/diffracted/reflected light detecting means for detecting light of the illuminated light scattered/diffracted/reflected at the illustrated spot and converting the detected light to an electric signal; an A/D converting means for converting the electric signal to digital data; an inspection coordinate detecting means for detecting a position on the surface of the object during inspection as inspection coordinate data at a time corresponding to the converted digital data; a particle/defect determining means for determining presence of a particle or a defect on the surface of the inspection object or in an interior of the inspection object close to its surface on the basis of the electric signal or the digital data; a particle diameter calculating means for calculating a size of the determined particle or defect on the basis of the digital data; and a particle/defect coordinate calculating means for calculating a position coordinate value of the particle or defect on the surface of the inspection object on the basis of information received from the inspection coordinate detecting unit, wherein the A/D converting means includes a digital data table for storing or saving a plurality of the digital data continuously obtained by continuously sampling the electric signal at intervals of a predetermined time on a main scan locus over a period of time corresponding at least 2 turns of the inspection object moving stage, the A/D converting means also includes an illustrated-spot illumination-distribution data table for storing or saving a relative illumination distribution of the illuminated light within the illustrated spot on the surface of the inspection object in a two-dimensional Cartesian coordinate system having a y axis corresponding to a direction of a straight line connected from a rotational center of the inspection object moving stage to a center of the illustrated spot and having an x axis perpendicular to the y axis as two-dimensional matrix data having data divisions divided at intervals of a first spacing in an x axis direction and at intervals of a second spacing in a y axis direction, and the particle/defect coordinate calculating means calculates position coordinate values X, Y of the determined particle or defect using a result of comparison between the digital data table and the illustrated-spot illumination-distribution data table in a two-dimensional Cartesian coordinate system (X,Y) having a Y axis corresponding to a direction of a linear symmetric axis on the surface of the inspection object and having an X axis perpendicular to the Y axis. The above expression "a plurality of said digital data continuously obtained by continuously sampling said electric signal on a main scan locus over a period of time corresponding at least 2 turns of the inspection object moving stage" means to use data about a plurality of turns of r in the (r,θ) coordinate system, for example, in order to identify a particle coordinate in a (x,y) two-dimensional plane. Further, the digital data table as an example of the memory for storing the data may have such a capacity as to be capable of storing all data occurred during that. Or when the capacity of the memory is not so large as to store all the data, the memory may have such a capacity as to be capable of storing only necessary skipped data about the vicinity of the particle.

Feature 2: A particle/defect detecting method according to the above Feature 1, wherein the particle diameter calculating means calculates a size of the particle or defect using a result of comparison between the digital data table and the illustrated-spot illumination-distribution data table.

Feature 3: A particle/defect detecting method according to the above Feature 1 or 2, wherein the particle/defect determining means determines the presence of the particle or defect by comparing the electric signal with a threshold.

Feature 4: A particle/defect detecting method according to the above Feature 1 or 2, wherein the particle/defect determining means determines the presence of the particle or defect using digital data from the A/D converting means or using digital data stored in the digital data table.

Feature 5: A particle/defect detecting method including: an inspection object moving stage nearly continuously moved in both main scan and sub-scan directions for providing a rotational motion in main scan and a translational motion in sub-scan; a light source; an illumination means for illuminating a surface of an object to be inspected with light from the light source as an illustrated spot of a predetermined size; a scattered/diffracted/reflected light detecting means for detecting light of the illuminated light scattered/diffracted/reflected at the illustrated spot and converting the detected light to an electric signal; an A/D converting means for converting the electric signal to digital data; an inspection coordinate detecting means for detecting a position on the surface of the object during inspection as inspection coordinate data at a time corresponding to the converted digital data; a particle/defect determining means for determining presence of a particle or a defect on the surface of the inspection object or in an interior of the inspection object close to its surface on the basis of the electric signal or the digital data; a particle diameter calculating means for calculating a size of the determined particle or defect on the basis of the digital data; and a particle/defect coordinate calculating means for calculating a position coordinate value of the particle or defect on the surface of the inspection object on the basis of information received from the inspection coordinate detecting means, wherein the A/D converting means includes a digital data table for storing or saving partial data extracted based on information from the particle/defect determining means, from a plurality of the digital data continuously obtained by continuously sampling the electric signal at intervals of a predetermined time on a main scan locus over a period of time corresponding at least 2 turns of the inspection object moving stage, the A/D converting means also includes an illustrated-spot illumination-distribution data table for storing or saving a relative illumination distribution of the illuminated light within the illustrated spot on the surface of the inspection object in a two-dimensional Cartesian coordinate system having a y axis corresponding to a direction of a straight line connected from a rotational center of the inspection object moving stage to a center of the illustrated spot and having an x axis perpendicular to the y axis as two-dimensional matrix data having data divisions divided at intervals of a first spacing in an x axis direction and at intervals of a second spacing in a y axis direction, and the particle/defect coordinate calculating means calculates position coordinate values X,Y of the determined particle or defect using a result of comparison between the digital data table and the illustrated-spot illumination-distribution data table in a two-dimensional Cartesian coordinate system (X,Y) having a Y axis corresponding to a direction of a linear symmetric axis on the surface of the inspection object and having an X axis perpendicular to the Y axis.

Feature 6: A particle/defect detecting method according to the above Feature 5, wherein the particle diameter calculating means calculates the size of the particle or defect using a result of comparison between the digital data table and the illustrated-spot illumination-distribution data table.

Feature 7: A particle/defect detecting method according to the above Feature 5 or 6, wherein the particle/defect determining unit includes a means for comparing the electric signal with a threshold and determining detection of the particle or defect when the electric signal exceeds the threshold, and the partial data stored or saved in the digital data table includes digital data appearing earlier by at least one or more sampling intervals than digital data having a time when the particle/defect determining means determines that the electric signal exceeded the threshold and appearing later by at least one or more sampling intervals therethan and also includes the inspection coordinate data corresponding to the digital data.

Feature 8: A particle/defect detecting method according to the above Feature 5 or 6, wherein the particle/defect determining means includes a unit for comparing the digital data from the A/D converting means with a threshold and determining the detection of the particle or defect when the digital data exceeds the threshold, and the partial data stored or saved in the digital data table includes digital data appearing earlier by at least one or more sampling intervals than a time of the digital data when the particle/defect determining means determines that the digital data exceeded the threshold and appearing later by at least one or more sampling intervals therethan and also includes the inspection coordinate data corresponding to the digital data.

Feature 9: A particle/defect detecting method according to any of Features 1 to 8, wherein a data interval of data in the illustrated-spot illumination-distribution data table in the y axis direction is set at about 5 μm when converted to a distance on the surface of the inspection object. In other words, in order to secure a coordinate accuracy necessary for the particle detected by the surface inspection equipment of the present embodiment to be put in the display screen of a scanning electron microscope (SEM) when the operator review the particle using the SEM; the coordinate detection resolution is required not to be higher than that of the SEM. To this end, the coordinate detection resolution is set desirably at "5 μm or less". In general, the higher a resolution is the better the result is. In an practical case, however, it is meaningless even when the resolution of an observation optical system is remarkably increased, and the numbers of pixels of a CCD as an imaging element in horizontal and vertical directions have their limits. Thus when the resolution is increased, the field of view of the SEM becomes correspondingly narrower. For this reason, the lower limit of the resolution is set desirably at "nearly 1 μm"

Feature 10: A particle/defect detecting method according to any of Features 1 to 9, wherein a data interval of data in the illustrated-spot illumination-distribution data table in the y axis direction is selected so that a distance between 2 adjacent main scan locuses on the inspection object in the sub-scan direction is divisible by the aforementioned data interval.

Feature 11: A particle/defect detecting method according to any of the above Features 1 to 10, wherein the illumination means is arranged so that at least one of optical conditions of an illuminated spot diameter, an incident angle to the surface of the inspection object, a polarization state of the illuminated light, a wavelength of the light source, and an luminous intensity of the light source is varied into a plurality of states, and a plurality of such illustrated-spot illumination-distribution data tables are provided so as to store or save a plurality of such illustrated spot illumination distributions corresponding to the plurality of optical conditions.

Feature 12: A particle/defect detecting method according to the above Feature 11, wherein one of the plurality of illustrated-spot illumination-distribution data tables stored or saved corresponding to the selected optical conditions is automatically selected according to the selected optical conditions upon inspection to be used upon the inspection.

Feature 13: A particle/defect detecting method according to any of the above Features 1 to 10, wherein an illustrated spot observation camera is provided to measure the relative illumination distribution within the illustrated spot, and the relative illumination distribution of the illuminated light within the illustrated spot measured by the illustrated spot observation camera is stored or saved in the illustrated-spot illumination-distribution data table as two-dimensional matrix data.

Feature 14: A particle/defect detecting method according to any of the above Features 1 to 10, wherein an illustrated spot observation camera is provided to measure the relative illumination distribution within the illustrated spot, and after the image resolution of the illustrated spot observation camera is changed, the relative illumination distribution of the illuminated light within the illustrated spot measured by the illustrated spot observation camera is stored or saved in the illustrated-spot illumination-distribution data table as two-dimensional matrix data.

Feature 15: A particle/defect detecting method according to the above Feature 11 or 12, wherein an illustrated spot observation camera is provided to measure the relative illumination distribution within the illustrated spot, and the relative illumination distribution of the illuminated light within the illustrated spot measured by the illustrated spot observation camera is stored or saved in the illustrated-spot illumination-distribution data table as two-dimensional matrix data.

Feature 16: A particle/defect detecting method according to the above Feature 11 or 12, wherein an illustrated spot observation camera is provided to measure the relative illumination distribution within the illustrated spot, and after the image resolution of the illustrated spot observation camera is changed, the relative illumination distribution of the illuminated light within the illustrated spot measured by the illustrated spot observation camera is stored or saved in the illustrated-spot illumination-distribution data table as two-dimensional matrix data.

Feature 17: A particle/defect detecting method according to the above Feature 11 or 12, wherein a within-illustratedspot illumination distribution measuring means is provided to measure the relative illumination distribution within the illustrated spot with use of the inspection object having a standard particle deposited thereon, and the relative illumination distribution of the illuminated light within the illustrated spot measured by the within-illustrated-spot illumination distribution measuring unit is stored or saved in the illustrated-spot illumination-distribution data table as two-dimensional matrix data.

Feature 18: A particle/defect detecting method according to any of the above Features 1 to 10, 13, and 14, wherein an illustrated spot illumination distribution is measured by the illustrated spot observation camera for each inspection object to be inspected or for each group of a plurality of inspection objects to be continuously inspected according to the same recipe, and the measured illustrated spot illumination distribution is stored or saved in the illustrated-spot illumination-distribution data table.

Feature 19: Particle/defect inspection equipment for inspecting a particle or a defect present on a surface of an object to be inspected or in interior of the object close to the surface including: an inspection object moving stage for providing a translational motion in its main scan and a translational motion as its sub-scan in a direction nearly perpendicular to the translational motion or providing a rotational motion as its main scan and a translational motion as its sub-scan; a light source; an illumination optical system for illuminating the surface of the inspection object with light from the light source as an illustrated spot having a predetermined size; a scattered/diffracted/reflected light detecting system for detecting light of the illuminated light scattered/diffracted/reflected at the illustrated spot and converting the detected light to an electric signal; an A/D converter for converting the electric signal to digital data; an inspection coordinate detecting mechanism for detecting as inspection coordinate data a position on the surface of the inspection object during inspection at a time corresponding to the converted digital data; a particle/defect determining mechanism for determining presence of the particle or defect on the basis of the electric signal or the digital data; a particle diameter calculation mechanism for calculating a size of the determined particle or defect on the basis of the digital data; and a particle/defect coordinate calculating mechanism for calculating a position coordinate value of the particle or defect on the surface of the inspection object on the basis of information from the inspection coordinate detecting mechanism, wherein the A/D converter includes a digital data table for continuously storing or saving a plurality of the digital data obtained by continuously sampling the electric signal at intervals of a predetermined time on a main scan locus over a period of time corresponding at least 2 turns of the inspection object moving stage and also includes an illustrated-spot illumination-distribution data table for storing or saving a relative illumination distribution of the illuminated light within the illustrated spot on the surface of the inspection object in a two-dimensional Cartesian coordinate system having a y axis in a direction of a straight line connected from a rotational center of the inspection object moving stage to a center of the illustrated spot and having an x axis perpendicular to the y axis as two-dimensional matrix data having data divisions divided at intervals of a first spacing in an x axis direction and at intervals of a second spacing in a y axis direction, and the particle/defect coordinate calculating mechanism calculates position coordinate values X, Y of the determined particle or defect using a result of comparison between the digital data table and the illustrated-spot illumination-distribution data table in a two-dimensional Cartesian coordinate system (X,Y) having a Y axis corresponding to a direction of a linear symmetric axis on the surface of the inspection object and having an X axis perpendicular to the Y axis.

Feature 20: A particle/defect inspection equipment according to the above Feature 19, wherein the particle diameter calculation mechanism calculates a size of the particle or defect using a result of comparison between the digital data table and the illustrated-spot illumination-distribution data table.

Feature 21: A particle/defect inspection equipment according to the above Feature 19 or 20, wherein the particle/defect determining mechanism determines the presence of the particle or defect by comparing the electric signal with a threshold.

Feature 22: A particle/defect inspection equipment according to the above Feature 19 or 20, wherein the particle/defect determining mechanism determines the presence of the particle or defect using digital data from the A/D converter or using the digital data stored in the digital data table.

Feature 23: Particle/defect inspection equipment for inspecting a particle or a defect present on a surface of an object to be inspected or in interior of the object close to the surface including: an inspection object moving stage for providing a translational motion in its main scan and a translational motion as its sub-scan in a direction nearly perpendicular to the translational motion or providing a rotational motion as its main scan and a translational motion as its sub-scan; a light source; an illumination optical system for illuminating the surface of the inspection object with light from the light source as an illustrated spot having a predetermined size; a scattered/diffracted/reflected light detecting system for detecting light of the illuminated light scattered/diffracted/reflected at the illustrated spot and converting the detected light to an electric signal; an A/D converter for converting the electric signal to digital data; an inspection coordinate detecting mechanism for detecting as inspection coordinate data a position on the surface of the inspection object during inspection at a time corresponding to the converted digital data; a particle/defect determining mechanism for determining presence of the particle or defect on the basis of the electric signal or the digital data; a particle diameter calculation mechanism for calculating a size of the determined particle or defect on the basis of the digital data; and a particle/defect coordinate calculating mechanism for calculating a position coordinate value of the particle or defect on the surface of the inspection object on the basis of information from the inspection coordinate detecting mechanism, wherein the A/D converter includes a digital data table for storing or saving partial data extracted based on information from the particle/defect determining unit, from a plurality of the digital data continuously obtained by continuously sampling the electric signal at intervals of a predetermined time on a main scan locus over a period of time corresponding at least 2 turns of the inspection object moving stage, the A/D converting means also includes an illustrated-spot illumination-distribution data table for storing or saving a relative illumination distribution of the illuminated light within the illustrated spot on the surface of the inspection object in a two-dimensional Cartesian coordinate system having a y axis in a direction of a straight line connected from a rotational center of the inspection object moving stage to a center of the illustrated spot and having an x axis perpendicular to the y axis as two-dimensional matrix data having data divisions divided at intervals of a first spacing in an x axis direction and at intervals of a second spacing in a y axis direction, and the particle/defect coordinate calculating mechanism calculates a position coordinate value X, Y of the determined particle or defect using a result of comparison between the digital data table and the illustrated-spot illumination-distribution data table in a two-dimensional Cartesian coordinate system (X,Y) having a Y axis corresponding to a direction of a linear symmetric axis on the surface of the inspection object and having an X axis perpendicular to the Y axis.

Feature 24: Particle/defect inspection equipment according to the above Feature 23, wherein the particle diameter calculation mechanism calculates the size of the particle or defect using a result of comparison between the digital data table and the illustrated-spot illumination-distribution data table.

Feature 25: Particle/defect inspection equipment according to the above Feature 23 or 24, wherein the particle/defect determining mechanism includes a comparison circuit for comparing the electric signal with a threshold and determining the detection of the particle or defect when the electric signal exceeds the threshold, and the partial data stored or saved in the digital data table includes digital data appearing earlier by at least one or more sampling intervals than digital data having a time when the particle/defect determining mechanism determines that the electric signal exceeded the threshold and appearing later by at least one or more sampling intervals therethan and also includes the inspection coordinate data corresponding to the digital data.

Feature 26: Particle/defect detecting equipment according to the above Feature 23 or 24, wherein the particle/defect determining mechanism includes a mechanism for comparing the digital data from the A/D converting means with a threshold and determining the detection of the particle or defect when the digital data exceeds the threshold, and the partial data stored or saved in the digital data table includes digital data appearing earlier by at least one or more sampling intervals than a time of the digital data when the particle/defect determining means determines that the digital data exceeded the threshold and appearing later by at least one or more sampling intervals therethan and also includes the inspection coordinate data corresponding to the digital data.

Feature 27: Particle/defect inspection equipment according to any of the above Features 19 to 26, wherein a data interval of data in the illustrated-spot illumination-distribution data table in the y axis direction is set at nearly 5 µm or less when converted to a distance on the surface of the inspection object.

Feature 28: Particle/defect inspection equipment according to any of the above Features 19 to 27, wherein an data interval of data in the illustrated-spot illumination-distribution data table in the y axis direction is selected so that a distance between adjacent 2 main scan locuses on the surface of the inspection object in the sub-scan direction is nearly divisible by the aforementioned data interval.

Feature 29: Particle/defect inspection equipment according to any of the above Features 19 to 28, wherein the illumination optical system is arranged so that at least one of optical conditions, that is, an illustrated spot diameter, an incident angle to the surface of the inspection object, a polarization state of the illuminated light, a wavelength of the light source, and a luminous intensity of the light source is changed to a plurality of states; a plurality of such illustrated-spot illumination-distribution data tables are provided; and a plurality of such illustrated spot illumination distributions corresponding to the plurality of optical conditions are stored or saved in the tables.

Feature 30: Particle/defect inspection equipment according to the above Feature 29, wherein one of the plurality of stored or saved illustrated-spot illumination-distribution data tables corresponding to the selected optical conditions is automatically selected according to the selected optical conditions upon inspection and used upon the inspection.

Feature 31: Particle/defect inspection equipment according to any of the above Features 19 to 28, wherein an illustrated spot observation camera is provided to measure a relative illumination distribution within the illustrated spot, and the relative illumination distribution of the illuminated light within the illustrated spot measured by the illustrated spot observation camera is stored or saved in the illustrated-spot illumination-distribution data table as two-dimensional matrix data.

Feature 32: Particle/defect inspection equipment according to the above Features 19 to 28, wherein an illustrated spot observation camera is provided to measure a relative illumination distribution within the illustrated spot, and, after the image resolution of the illustrated spot observation camera is changed, the relative illumination distribution of the illuminated light within the illustrated spot measured by the illustrated spot observation camera is stored or saved in the illustrated-spot illumination-distribution data table as two-dimensional matrix data.

Feature 33: Particle/defect inspection equipment according to the above Feature 29 or 30, an illustrated spot observation camera is provided to measure a relative illumination distribution within the illustrated spot, an the relative illumination distribution of the illuminated light within the illustrated spot measured by the illustrated spot observation camera is stored or saved in the illustrated-spot illumination-distribution data table as two-dimensional matrix data.

Feature 34: Particle/defect inspection equipment according to the above Feature 29 or 30, wherein an illustrated spot observation camera is provided to measure a relative illumination distribution within the illustrated spot and, after the image resolution of the illustrated spot observation camera is changed, the relative illumination distribution of the illuminated light within the illustrated spot measured by the illustrated spot observation camera is stored or saved in the illustrated-spot illumination-distribution data table as two-dimensional matrix data.

Feature 35: Particle/defect inspection equipment according to the above Feature 29 or 30, wherein the equipment has a function of a within-illustrated spot illumination distribution measuring function of measuring a relative illumination distribution within the illustrated spot with use of the inspection object having a standard particle deposited thereon, and the relative illumination distribution of the illuminated light within the illustrated spot measured by the within-illustrated spot illumination distribution measuring function is stored or saved in the illustrated-spot illumination-distribution data table as two-dimensional matrix data.

Feature 36: Particle/defect inspection equipment according to any of the above Feature 19 to 28, 21, and 32, wherein an illustrated spot illumination distribution is measured by the illustrated spot observation camera for each inspection object to be inspected or for each group of a plurality of inspection objects to be continuously inspected according to the same recipe, and the measured illustrated spot illumination distribution is stored or saved in the illustrated-spot illumination-distribution data table.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus which detects an anomaly of a substrate comprising;
   an illuminating unit which supplies light and forms an illumination spot on said substrate;
   a detection unit which detects light from said illumination spot; and
   a processing unit, wherein said processing unit:
      acquires digital data expressed by (r, θ) coordinate system by using detection result of said detection unit, and
      acquires digital data expressed by two-dimensional Cartesian coordinate system by using a relative illumination distribution of said illumination spot, and said digital data expressed by (r, θ) coordinate system.

2. An inspection apparatus according claim 1, wherein said relative illumination distribution is expressed by two-dimensional Cartesian coordinate system.

3. An inspection apparatus according claim 1, wherein said processing unit acquires position of said anomaly on said two-dimensional Cartesian coordinate system.

4. An inspection apparatus according claim 1, further comprising:
   a changing unit which changes an optical condition of said illumination unit;
   a memory which stores a plurality of relative illumination distributions corresponding to a plurality of optical conditions; and
   a selecting unit which selects a relative illumination distribution corresponding to said optical condition changed by said changing unit from said relative illumination distributions.

5. An inspection apparatus according to claim 1, wherein said processing unit corrects a tilt of said anomaly.

6. A method for detecting an anomaly of a substrate, the method comprising steps of:
   illuminating light on said substrate to form an illumination spot on said substrate;
   detecting light from said illumination spot;
   acquiring digital data expressed by (r, θ) coordinate system by using said detection result, and
   acquiring digital data expressed by two-dimensional Cartesian coordinate system by using a relative illumination distribution of said illumination spot, and said digital data expressed by (r, θ) coordinate system by a processing unit.

7. A method according to claim 6, wherein said relative illumination distribution is expressed by two-dimensional Cartesian coordinate system.

8. A method according to claim 6, further comprising:
   acquiring position of said anomaly on said two-dimensional Cartesian coordinate system.

9. A method according to claim 6, further comprising
   changing an optical condition of said illumination of light;
   storing a plurality of relative illumination distributions corresponding to a plurality of optical conditions; and
   selecting a relative illumination distribution corresponding to said changed optical condition from said relative illumination distributions.

10. A method according to claim 6, further comprising:
    correcting a tilt of said anomaly.

* * * * *